United States Patent
Husseiny Elsayed et al.

(10) Patent No.: US 10,206,984 B2
(45) Date of Patent: *Feb. 19, 2019

(54) **ATTENUATED *SALMONELLA* BACTERIA AND METHODS OF USING**

(71) Applicant: CITY OF HOPE, Duarte, CA (US)

(72) Inventors: Mohamed I. Husseiny Elsayed, Torrance, CA (US); Kevin Ferreri, Los Angeles, CA (US)

(73) Assignee: CITY OF HOPE, Duarte, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/583,776

(22) Filed: May 1, 2017

(65) Prior Publication Data
US 2017/0368156 A1    Dec. 28, 2017

Related U.S. Application Data

(63) Continuation of application No. 14/777,415, filed as application No. PCT/US2014/029591 on Mar. 14, 2014, now Pat. No. 9,636,386.

(60) Provisional application No. 61/798,176, filed on Mar. 15, 2013.

(51) Int. Cl.
| | |
|---|---|
| *A61K 39/112* | (2006.01) |
| *A61K 49/00* | (2006.01) |
| *A61K 48/00* | (2006.01) |
| *A61K 39/00* | (2006.01) |
| *A61K 35/74* | (2015.01) |
| *A61K 39/39* | (2006.01) |
| *A61K 35/00* | (2006.01) |

(52) U.S. Cl.
CPC .......... *A61K 39/0008* (2013.01); *A61K 35/74* (2013.01); *A61K 39/39* (2013.01); *A61K 2035/11* (2013.01); *A61K 2039/522* (2013.01); *A61K 2039/523* (2013.01); *A61K 2039/542* (2013.01); *A61K 2039/55516* (2013.01)

(58) Field of Classification Search
CPC ..... A61K 39/00; A61K 39/0275; A61K 47/00
USPC .......... 424/9.1, 9.2, 93.1, 93.2, 93.4, 234.1, 424/258.1, 278.1
See application file for complete search history.

(56) References Cited

U.S. PATENT DOCUMENTS

| | | | |
|---|---|---|---|
| 9,636,386 B2* | 5/2017 | Husseiny Elsayed | ...................... A61K 39/0008 |
| 2006/0257412 A1 | 11/2006 | Bowdish et al. | |
| 2008/0075739 A1 | 3/2008 | Hensel et al. | |
| 2008/0108585 A1 | 5/2008 | Steinman et al. | |
| 2008/0248066 A1 | 10/2008 | Dubensky et al. | |
| 2012/0107301 A1 | 5/2012 | Bowdish et al. | |

OTHER PUBLICATIONS

Abrahams, G. L., et al., "Manipulating Cellular Transport and Immune Responses: Dynamic Interactions Between Intracellular *Salmonella enterica* and Its Host Cells," Cell. Microbiol. 8(5):728-737 (2006).
Amatuzio, D. S., et al., "Interpretation of the Rapid Intravenous Glucose Tolerance Test in Normal Individuals and in Mild Diabetes Mellitus," J. Clin. Invest. 32:428-435 (1953).
Andrikopoulos, S., et al., "Evaluating the Glucose Tolerance Test in Mice," Am. J. Physiol. Endocrinol. Metab. 295:E1323-E1332 (2008).
Attridge, S.R., et al., "Oral Delivery of Foreign Antigens by Attenuated *Salmonella*: Consequences of Prior Exposure to the Vector Strain," Vaccine 15(2):155-162 (1997).
Balasa, B., et al., "Islet-Specific Expression of IL-10 Promotes Diabetes in Nonobese Diabetic Mice Independent of Fas, Perforin, TNF Receptor-1, and TNF Receptor-2 Molecules," J. Immunol. 165:2841-2849 (2000).
Balasa, B., et al., "A Mechanism for IL-10-Mediated Diabetes in the Nonobese Diabetic (NOD) Mouse: ICAM-1 Deficiency Blocks Accelerated Diabetes," J. Immunol. 165:7330-7337 (2000).
Bao, J. X., et al., "Prior Immunologic Experience Potentiates the Subsequent Antibody Response When *Salmonella* Strains Are Used as Vaccine Carriers," Infect. Immun. 59(10):3841-3845 (1991).
Cheminay, C., et al., "Rational Design of *Salmonella* Recombinant Vaccines," Int. J. Med. Microbiol. 298:87-98 (2008).
Clemente-Casares, X., et al., "Antigen-Specific Therapeutic Approaches in Type 1 Diabetes," Cold Spring Harb. Perspect. Med. 4:a007773 (2012).
Coombes, B. K., et al., "Expression and Secretion of *Salmonella* Pathogenicity Island-2 Virulence Genes in Response to Acidification Exhibit Differential Requirements of a Functional Type III Secretion Apparatus and SsaL," J. Biol. Chem. 279(48):49804-49815 (2004).
Coombes, J. L., et al., "A Functionally Specialized Population of Mucosal CD103+ DCs Induces Foxp3+ Regulatory T Cells Via a TGF-Beta—and Retinoic Acid-Dependent Mechanism," J. Exp. Med. 204(8):1757-1764 (2007).
Coombes, J. L., et al., "Dendritic Cells in Intestinal Immune Regulation," Nat. Rev. Immunol. 8(6):435-446 (2008).
Curtiss, R., et al., "New Technologies in Using Recombinant Attenuated *Salmonella* Vaccine Vectors," Crit. Rev. Immunol. 30(3):255-270 (2010).
Deiwick, J., et al., "Environmental Regulation of *Salmonella* Pathogenicity Island 2 Gene Expression," Mol. Microbiol. 31:1759-1773 (1999).
Delong, T., et al., "Islet Amyloid Polypeptide Is a Target Antigen for Diabetogenic CD4+ T Cells," Diabetes 60:2325-2330 (2011).
Denes, B., et al., "Autoantigens Plus Interleukin-10 Suppress Diabetes Autoimmunity," Diabetes Technol. Ther. 12(8):649-661 (2010).
Denes, B., et al., "Suppression of Hyperglycemia in NOD Mice After Inoculation with Recombinant Vaccinia Viruses," Mol. Biotechnol. 34:317-327 (2006).
Evans, D. T., et al., "Mucosal Priming of Simian Immunodeficiency Virus-Specific Cytotoxic T-Lymphocyte Responses in Rhesus Macaques by the *Salmonella* Type III Secretion Antigen Delivery System," J. Virol. 77(4):2400-2409 (2003).

(Continued)

*Primary Examiner* — Rodney P Swartz
(74) *Attorney, Agent, or Firm* — Perkins Coie LLP

(57) ABSTRACT

Provided herein are attenuated *Salmonella* bacteria for expressing autoantigen alone or in combination with an immunomodulatory, as well as methods of using these bacteria to treat various autoimmune disorders.

6 Claims, 11 Drawing Sheets

Specification includes a Sequence Listing.

(56) References Cited

OTHER PUBLICATIONS

Forrest, B. D., "Impairment of Immunogenicity of *Salmonella* Typhi Ty21a Due to Preexisting Cross-Reacting Intestinal Antibodies," J. Infect. Dis. 166:210-212 (1992).
Galan, J. E., et al., "Cloning and Characterization of the asd Gene of *Salmonella typhimurium*: Use in Stable Maintenance of Recombinant Plasmids in *Salmonella* Vaccine Strains," Gene 94:29-35 (1990).
Gentschev, I., et al., "Vivotif—A 'Magic Shield' for Protection Against Typhoid Fever and Delivery of Heterologous Antigens," Chemotherapy 53:177-180 (2007).
Goudy, K. S., et al., Systemic Overexpression of IL-10 Induces CD4+ CD25+ Cell Populations In Vivo and Ameliorates Type 1 Diabetes in Nonobese Diabetic Mice in a Dose-Dependent Fashion, J. Immunol. 171:2270-2278 (2003).
Grangette, C., et al., "Protection Against Tetanus Toxin After Intragastric Administration of Two Recombinant Lactic Acid Bacteria: Impact of Strain Viability and In Vivo Persistence," Vaccine 20:3304-3309 (2002).
Hegazy, W. A. H., et al., "Evaluation of *Salmonella enterica* Type III Secretion System Effector Proteins as Carriers for Heterologous Vaccine Antigens," Infect. Immun. 80(3):1193-1202 (2012).
Herold, K. C., et al., "Teplizumab Treatment May Improve C-Peptide Responses in Participants with Type 1 Diabetes After the New-Onset Period: A Randomised Controlled Trial," Diabetologia 56(2):391-400 (2013).
Hjorth, M., et al., "GAD-Alum Treatment Induces GAD65-Specific CD4+ CD25high FOXP3+ Cells in Type 1 Diabetic Patients," Clin. Immunol. 138:117-126 (2011).
Holmgren, J., et al., "Mucosal Immunity and Vaccines," Nat. Med. Suppl. 11(4):545-553 (2005).
Hulme, M. A., et al., "Central Role for Interleukin-2 in Type 1 Diabetes," Diabetes 61:14-22 (2012).
Husseiny, M. I., et al., "Rapid Method for the Construction of *Salmonella enterica* Serovar Typhimurium Vaccine Carrier Strains," Infect. Immun. 73(3):1598-1605 (2005).
Husseiny, M. I., et al., "Construction of Highly Attenuated *Salmonella enterica* Serovar Typhimurium Live Vectors for Delivering Heterologous Antigens by Chromosomal Integration," Microbiol. Res. 163:605-615 (2008).
Husseiny, M. I., et al., "Evaluation of an Intracellular-Activated Promoter for the Generation of Live *Salmonella* Recombinant Vaccines," Vaccine 23:2580-2590 (2005).
Husseiny, M. I., et al., "Recombinant Vaccines Based on Translocated Effector Proteins of *Salmonella* Pathogenicity Island 2," Vaccine 25:185-193 (2007).
Husseiny, M. I., et al., "Evaluation of *Salmonella* Live Vaccines with Chromosomal Expression Cassettes for Translocated Fusion Proteins," Vaccine 27:3780-3787 (2009).
Jaensson, E., et al., "Small Intestinal CD103+ Dendritic Cells Display Unique Functional Properties that are Conserved Between Mice and Humans," J. Exp. Med. 205(9):2139-2149 (2008).
Kantele, A., et al., "Active Immunity is Seen as a Reduction in the Cell Response to Oral Live Vaccine," Vaccine 9(6):428-431 (1991).
Ludvigsson, J., "Therapy with GAD in Diabetes," Diabetes Metab. Res. Rev. 25:307-315 (2009).
Ludvigsson, J., et al., "The Role of Immunomodulation Therapy in Autoimmune Diabetes," J. Diabetes Sci. Technol. 3(2):320-330 (2009).
Ludvigsson, J., et al., "GAD Treatment and Insulin Secretion in Recent-Onset Type 1 Diabetes," New Engl. J. Med. 359:1909-1920 (2008).
Malek, T. R., et al., "Tolerance, Not Immunity, Crucially Depends on IL-2," Nat. Rev. Immunol. 4:665-674 (2004).

Manuel, E. R., et al., "Enhancement of Cancer Vaccine Therapy by Systemic Delivery of a Tumor-Targeting *Salmonella*-Based STAT3 shRNA Suppresses the Growth of Established Melanoma Tumors," Cancer Res. 71:4183-4191 (2011).
Moser, A., et al., "Beta Cell Antigens in Type I Diabetes: Triggers in Pathogenesis and Therapeutic Targets," F1000 Biol. Rep. 2:75 (2010).
Nicholas, D., et al., "Autoantigen Based Vaccines for Type 1 Diabetes," Discov. Med. 11(59):293-301 (2011).
Nishikawa, H., et al., "In Vivo Antigen Delivery by a *Salmonella typhimurium* Type III Secretion System for Therapeutic Cancer Vaccines," J. Clin. Invest. 116(7):1946-1954 (2006).
Peakman, M., et al., "Antigen-Specific Immunotherapy for Type 1 Diabetes: Maximizing the Potential," Diabetes 59:2087-2093 (2010).
Pennline, K. J., et al., "Recombinant Human IL-10 Prevents the Onset of Diabetes in the Nonobese Diabetic Mouse," Clin. Immunol. Immunopathol. 71(2):169-175 (1994).
Raine, T., et al., *Salmonella typhimurium* Infection in Nonobese Diabetic Mice Generates Immunomodulatory Dendritic Cells Able to Prevent Type 1 Diabetes, J. Immunol. 177:2224-2233 (2006).
Saucier, G., et al., "Clinical Use of the Glucose Disappearance Rate," Canad. Med. Ass. J. 88: 1231-1237 (1963).
Saxena, M., et al., "Pre-Existing Immunity Against Vaccine Vectors—Friend or Foe?" Microbiology 159:1-11 (2013).
Sevil Domenech, V. E., et al., "Heterologous Prime-Boost Immunizations with Different *Salmonella* Serovars for Enhanced Antigen-Specific CD8 T-Cell Induction," Vaccine 26:1879-1886 (2008).
Stadinski, B. D., et al., "Chromogranin A is an Autoantigen in Type 1 Diabetes," Nat. Immunol. 11(3):225-231 (2010).
Sun, C.M., et al., "Small Intestine Lamina Propia Dendritic Cells Promote De Novo Generation of Foxp3 T Reg Cells Via Retinoic Acid," J. Exp. Med. 204(8):1775-1785 (2007).
Takiishi, T., et al., "Reversal of Autoimmune Diabetes by Restoration of Antigen-Specific Tolerance Using Genetically Modified Lactococcus Lactis in Mice," J. Clin. Invest. 122(5):1717-1725 (2012).
Todorov, I., et al., "Quantitative Assessment of Beta Cell Apoptosis and Cell Composition of Isolated, Undisrupted Human Islets by Laser Scanning Cytometry," Transplantation 90(8):836-842 (2010).
Turley, S. J., et al., "Endocrine Self and Gut Non-Self Intersect in the Pancreatic Lymph Nodes," Proc Natl Acad Sci USA 102(49):17729-17733 (2005).
United States Patent and Trademark Office, International Search Report and Written Opinion dated Aug. 11, 2014 for PCT/US2014/029591.
Vindurampulle, C. J., et al., "Impact of Vector Priming on the Immunogenicity of Recombinant *Salmonella* Vaccines," Infection and Immunity 71(1):287-297 (2003).
Von Herrath, M., et al., "Progress in Immune-Based Therapies for Type 1 Diabetes," Clin. Exp. Immunol. 172:186-202 (2013).
Weiner, H. L., "Oral Tolerance," Immunol. Rev. 241(1):241-259 (2011).
Wherrett, D. K., et al., "Antigen-Based Therapy with Glutamic Acid Decarboxylase (GAD) Vaccine in Patients with Recent-Onset Type 1 Diabetes: A Randomised Double-Masked Controlled Trial," Lancet 378(9788):319-327 (2011).
Xiong, G., et al., "Novel Cancer Vaccine Based on Genes of *Salmonella* Pathogenicity Island 2," Int. J. Cancer 126(11)L2622-2634 (2010).
Xu, X., et al., "Efficacy of Intracellular Activated Promoters for Generation of *Salmonella*-Based Vaccines," Infection and Immunity 78(11):4828-4838 (2010).
Yang, J., et al., "Islet-Specific Glucose-6-Phosphatase Catalytic Subunit-Related Protein-Reactive CD4+ T Cells in Human Subjects," J. Immunol. 176:2781-2789 (2006).
Zhang, L., et al., "Insulin as an Autoantigen in NOD/HUman Diabetes," Curr. Opin. Immunol. 20(1):111-118 (2008).

* cited by examiner

A) Control infection with *Salmonella*

B) Expression of autoantigens and translocation by SPI2-T3SS of *Salmonella*

Sal-PPI
(Pro sseA sscB sseF::Ins2::MycDDK)

Sal-GAD65
(Pro sseA sscB sseF::GAD2::MycDDK)

C) Expression of tolerogenic cytokines by host cells

Sal/TGFβ
(Pro CMV Tgfb1::MycDDK)

Sal/IL10
(Pro CMV Il10::MycDDK)

A.

B.

C.

A.

B.

C.

A.

B.

A.

B.

SEQUENCE LISTING

```
<160> NUMBER OF SEQ ID NOS: 3

<210> SEQ ID NO 1
<211> LENGTH: 28
<212> TYPE: DNA
<213> ORGANISM: Artificial Sequence
<220> FEATURE:
<223> OTHER INFORMATION: PCR primer

<400> SEQUENCE: 1
atagttaaca tagggcggcc gggaattc                                              28

<210> SEQ ID NO 2
<211> LENGTH: 35
<212> TYPE: DNA
<213> ORGANISM: Artificial Sequence
<220> FEATURE:
<223> OTHER INFORMATION: PCR primer

<400> SEQUENCE: 2
tcgtctagat taaaccttat cgtcgtcatc cttgt                                      35

<210> SEQ ID NO 3
<211> LENGTH: 28
<212> TYPE: DNA
<213> ORGANISM: Artificial Sequence
<220> FEATURE:
<223> OTHER INFORMATION: PCR primer

<400> SEQUENCE: 3
atagttaaca tggcatctcc gggctctg                                              28
```

ATTENUATED *SALMONELLA* BACTERIA AND METHODS OF USING

PRIORITY CLAIM

This application is a continuation of U.S. application Ser. No. 14/777,415, filed Mar. 14, 2014, and issued as U.S. Pat. No. 9,636,386, which is a U.S. national phase application of International Application No. PCT/US14/29591, filed Mar. 14, 2014, which claims priority to U.S. Provisional Application No. 61/798,176, filed Mar. 15, 2013, all of which are incorporated herein by reference in their entirety, as if fully set forth herein.

BACKGROUND

Type 1 diabetes (T1D) is an autoimmune disease in which reaction to specific self-antigens results in the destruction of pancreatic insulin-producing β cells by antigen-specific antibodies and cytotoxic T lymphocytes (CTLs). There is no cure for T1D, and the only treatment options currently available are insulin and/or cell therapy. A variety of methods are currently under development for treating T1D by inhibiting autoimmunity. These include systemic immunosuppression, activation or inhibition of specific immune signaling pathways, and infusion of specific regulatory cell populations (Herold 2013; Coombes 2007).

One of the most promising approaches for preventing β cell autoimmune destruction is vaccination with diabetic autoantigens, which can result in inhibition of destructive islet-specific responses and induction of regulatory responses (Holmgren 2005; Peakman 2010; Nicholas 2011). In certain cases, autoantigen vaccination has been combined with administration of cytokines, which may synergize with the antigen-specific effect (Denes 2006; Denes 2010). The autoantigens proinsulin and GAD65 have both proven to be effective in reversing and preventing diabetes in non-obese diabetic (NOD) mouse models of T1D. However, human clinical trials using these autoantigens have been disappointing.

SUMMARY

The present application discloses novel compositions and methods for the treatment of autoimmune disorders such as T1D.

Provided herein in certain embodiments are attenuated *Salmonella* bacteria comprising a nucleic acid encoding an autoantigen under the control of an SPI2 promoter. In certain embodiments, the bacteria further comprises a nucleic acid encoding an immunomodulator.

Provided herein in certain embodiments are vaccine compositions and pharmaceutical formulations containing the *Salmonella* bacteria provided herein. In certain of these embodiments, the *Salmonella* bacteria comprise a nucleic acid encoding an autoantigen and a nucleic acid encoding an immunomodulator. In other embodiments, the *Salmonella* bacteria do not contain a nucleic acid encoding an immunomodulator. In certain of these embodiments, the composition or formulation further comprises one or more immunomodulators or one or more vectors comprising a nucleic acid encoding an immunomodulator.

Provided herein in certain embodiments are methods of treating autoimmune disorders by administering attenuated *Salmonella* bacteria comprising a nucleic acid encoding an autoantigen under the control of an SPI2 promoter and a nucleic acid encoding an immunomodulator. In certain of these embodiments, treatment results in modulation of the immune response, and in certain embodiments treatment results in vaccination against the autoimmune disorder.

Provided herein in certain embodiments are methods of treating autoimmune disorders by administering attenuated *Salmonella* bacteria comprising a nucleic acid encoding an autoantigen under the control of an SPI2 promoter and a second vector comprising a nucleic acid encoding an immunomodulator. In certain of these embodiments, treatment results in modulation of the immune response, and in certain embodiments treatment results in vaccination against the autoimmune disorder.

Provided herein in certain embodiments are methods of treating autoimmune disorders by administering attenuated *Salmonella* bacteria comprising a nucleic acid encoding a diabetic autoantigen under the control of an SPI2 promoter and further administering one or more immunomodulators. In certain of these embodiments, treatment results in modulation of the immune response, and in certain embodiments treatment results in vaccination against the autoimmune disorder.

DETAILED DESCRIPTION

Figure 1:
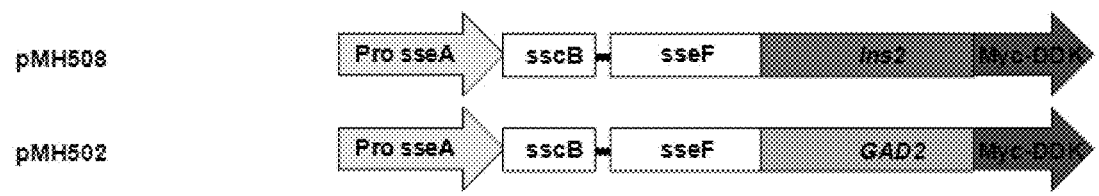
FIG. 1: Schematics of the autoantigen constructs pMH508 ($P_{ssrA}$ sscB sseF::Ins2::MycDDK) and pMH502 ($P_{ssrA}$ sscB sseF::Gad2::MycDDK) for expression and translocation of preproinsulin (PPI) and GAD65, respectively, by *Salmonella* SPI2-T3SS.

The following description of the invention is merely intended to illustrate various embodiments of the invention. As such, the specific modifications discussed are not to be construed as limitations on the scope of the invention. It will be apparent to one skilled in the art that various equivalents, changes, and modifications may be made without departing from the scope of the invention, and it is understood that such equivalent embodiments are to be included herein. All references cited herein are incorporated by reference in their entirety.

Vaccination with diabetic autoantigens represents a promising approach for the treatment of β cell autoimmunity. Many diabetic autoantigens have been identified (Moser 2010), including proinsulin (Zhang 2008), glutamic acid decarboxylase (GAD65 from the GAD2 gene) (Ludvigsson 2009a), islet-specific glucose-6-phosphatase (Yang 2006), chromogranin A (Stadinski 2010), and islet amyloid polypeptide (Delong 2011). The best characterized of these are proinsulin and GAD65, both of which have shown some ability to reverse and prevent diabetes in NOD mice. However, human clinical trial results for these autoantigens have been disappointing (von Herrath 2013; Clemente-Casares 2012). For example, vaccination with GAD-alum was found to induce regulatory T cells (Hjorth 2011) and delay the loss of glucose-stimulated C-peptide levels in subjects treated soon after diagnosis, but did not prevent the disease (Ludvigsson 2008; Ludvigsson 2009b; Wherret 2011).

Oral delivery of antigens has long been recognized as an effective route for induction of tolerizing effects. Gut-associated lymphoid tissue (GALT) is faced with massive levels of antigens both from the diet and from intestinal flora, and yet suppresses inappropriate escalation of the inflammatory response through a tendency towards tolerance (Holmgren 2005; Weiner 2011). This tendency has been exploited in the development of treatments for autoimmune diseases (Holmgren 2005).

An emerging method for safe and effective delivery of oral antigen-specific vaccines is the use of live attenuated (non-pathogenic) *Salmonella typhimurium* (Cheminay 2008). Infection with attenuated *S. typhimurium* has been shown previously to generate beneficial non-specific immune responses in NOD mice (Raine 2006). *Salmonella* carrying an antigen-expression plasmid are naturally transferred from the gut to phagosomes of GALT antigen presenting cells (APCs) where they form *Salmonella*-containing vacuoles (SCV). The bacteria remain viable and multiply inside the SCV and deliver the recombinant antigen into the host cell cytosol, thus avoiding intestinal degradation of antigen (Xiong 2010; Husseiny 2009; Husseiny 2007; Husseiny 2005). The APCs process and present the antigen to other immune cells in the gut, then migrate to other organs (Coombes 2008; Turley 2005). Such vaccines have been shown to be very effective in eliciting both CD8 and CD4 T cell-mediated immune responses in models of infectious diseases and cancer (Nishikawa 2006; Evans 2003). In fact, *Salmonella* is being used for the development of cancer vaccines with promising results, though maximum effectiveness requires addition of immunostimulatory agents to augment the cytotoxic effect (Xiong 2010; Manuel 2011).

Vaccination using *Salmonella* vectors typically results in the development of cytotoxic T cells (CTLs) and antigen-specific antibodies, and has been applied to several different model antigens as well as to certain cancer antigens which results in the destruction of the tumors by the CTLs. Beyond antigen expression, *Salmonella* can also be used as a DNA vaccine to deliver expression vectors that are directly expressed by the host cell (Curtiss 2010). In this modality, *Salmonella* vectors can be used to deliver intact immunomodulators to the site of antigen presentation. This *Salmonella*-based approach can accommodate various combinations of antigens and host-expressed modulators for optimization of treatment regimens. The flexibility of the system allows rapid development of new immunotherapies which provide robust and durable delivery of multiple antigens in a safe and inexpensive manner.

*Salmonella* pathogenicity island 2 (SPI2) is a virulence factor that encodes a type III secretion system (T3SS), as well as various proteins that function as transcriptional regulators and effector proteins inside host cells. Expression of SPI2 genes is regulated by several transcription factors, including an SsrA/SsrB two-component system encoded by the SPI2. SsrB binds multiple promoters of SPI2 genes encoding the T3SS and various effectors, including for example SseA-G and SscA-B. Infection of macrophages by Salmonella activates the SPI2 locus, allowing Salmonella to establish a replicative vacuole inside the host cell (Coombes 2004). Utilization of the SPI2-encoded T3SS (Abrahams 2006) for antigen delivery delays antigen expression until the bacteria are taken up by APCs, thereby increasing safety and efficacy. Live attenuated Salmonella vaccines using SPI2-T3SS have been developed previously for the treatment of certain cancers (either alone or in combination with various immunostimulatory agents), but these systems have never been evaluated as autoantigen-delivery vehicles for diabetes (Husseiny 2005a; Husseiny 2005b; Husseiny 2007; Husseiny 2008; Husseiny 2009; Xu 2010; Xiong 2010; Manuel 2011).

Other oral bacteria-based approaches are currently being explored as vectors for antigen-specific immunotherapies for diabetes. Most notably is the elegant study by Takiishi et alia (Takiishi 2012) using *Lactococcus lactis* to simultaneously deliver proinsulin and IL10. By co-administration of anti-CD3 the authors were able to induce antigen-specific tolerance and reverse early onset diabetes. However, a distinct advantage of *Salmonella* for vaccine development is that the antigen is only expressed after the bacteria are inside the host APCs due to the SPI2 promoter (Cheminay 2008). Bypassing expression of antigen in the intestinal lumen avoids degradation and loss of antigen, and also unwanted immune responses. Furthermore, internalization of *Salmonella* by dendritic cells ensures persistent antigen expression without dietary or other influences, which in the case of *Lactococcus* limits its ability to generate an antigen-specific response (Grangette 2002). Since it is internalized, *Salmonella*, unlike *Lactococcus*, can also carry and transfer mammalian expression vectors to be expressed by the host cells (Curtiss 2010), providing an efficient method for local secretion of immunomodulators such as TGFβ as provided herein.

Another benefit of using live bacteria for development of oral vaccines is the ease with which new vaccines can be generated and tested using standard molecular techniques. This allows investigation of several autoantigens alone and in combination, which may be beneficial for translation to human studies. As for translation to the clinic, *Salmonella*-based vaccines have proven safe and effective, and FDA-approved oral attenuated *Salmonella* vaccine is currently being produced by Berna Biotech (Switzerland) and available in the United States (Vivotif, Crucell Vaccines, Miami Lakes, Fla.) (Gentschev 2007).

A potential confounding factor is the development of an immune response against the vector (i.e. bacteria strain) used to deliver the heterologous antigen, which can suppress the response to booster treatments. This has been observed with *Salmonella typhi* Ty21A (Vivotif) vaccine and was suggested to result from suppression of bacterial multiplication, prevention of adhesion to the mucosa epithelium, and inhibition of invasion of the mucosa (Forrest 1992; Kantele 1991). Furthermore, pre-existing immunity, or pre-exposure to related strains, can also diminish the response to heterologous antigens delivered in the same or similar vectors (Attridge 1997). However, the effect appears to depend on several factors (Saxena 2013) including the strength of the response to the primary vaccination (Kantele 1991), as well as the specific strain and the specific antigen (Vindurampulle 2003), and in some cases prior exposure to the vector enhances the response to the heterologous antigen (Bao 1991). Nevertheless, an effective strategy to overcome this limitation is to prime using one strain and boost with another strain expressing the same antigen. Sevil Domènech et. al (Sevil Domenech 2008) have demonstrated that this approach was effective even using *Salmonella typhimurium* (antigen O group B) followed by *Salmonella dublin* (antigen O group D), and vice versa. Still, all of these studies examined the immune response to protective vaccines, so the effect of pre-exposure in the context of a tolerogenic vaccine will have to be investigated.

As disclosed herein, a novel attenuated *Salmonella* bacterium has been developed and evaluated as a vector for the oral delivery of diabetic autoantigens. This bacterium was developed by inserting nucleic acids encoding various diabetic autoantigens into *Salmonella typhimurium* strain MvP728, which has been used previously as a vector for the delivery of tumor-associated antigens and found to be non-toxic to mice and capable of effectively expressing and translocating proteins inside the cytosol of murine macrophages. Expression of the diabetic autoantigen is controlled by an SPI2 promoter. Since the SPI2 promoter of *Salmonella* is only active inside a host cell, placing autoantigen expression under control of the SPI2 promoter insures that the resultant bacterium preferentially delivers autoantigen into the cytosol of APCs for optimal immunogenicity. Oral administration of these bacteria in a NOD mouse T1D model was found to reduce glucose levels, and to prevent the onset of diabetes when administered in combination with vectors expressing immunomodulators. NOD mice are commonly used for initial pre-clinical studies of diabetes treatment because they exhibit many similarities in cell populations, autoantibody production, and disease etiology to human T1D. Based on these findings, the present application provides novel compositions and methods for the treatment or prevention of autoimmune disorders such as T1D.

Provided herein in certain embodiments are attenuated *Salmonella* bacteria comprising an exogenous nucleic acid sequence encoding an autoantigen or a portion thereof under the control of an SPI2 promoter. These *Salmonella* bacteria are interchangeably referred to herein as *Salmonella* vectors, as they function to introduce an exogenous autoantigen into a host cell in a manner that results in autoantigen expression. In certain embodiments of the attenuated *Salmonella* bacteria provided herein, the autoantigen is a diabetic autoantigen, and in certain of these embodiments the diabetic autoantigen is selected from the group consisting of proinsulin, glutamic acid decarboxylase, islet-specific glucose-6-phosphatase, chromogranin A, islet amyloid polypeptide, heat shock protein 60, islet antigen 2, and zinc transporter-8. In certain embodiments, the exogenous nucleic acid sequence encodes a complete diabetic autoantigen. In other embodiments, the autoantigen may be expressed in a truncated or mutated form, for example with one or more missing N- or C-terminal residues versus a wild-type version of the autoantigen or as a single concatenated antigenic region or peptide.

A variety of SPI2 promoters are known in the art. Examples of suitable SPI2 promoters for use in the attenuated *Salmonella* bacteria provided herein include the SPI2-T3SS promoters ssaG, sseA, sseJ, sifA, and sifB (Xu 2010). In certain embodiments, autoantigen expression can be increased by using a stronger SPI2 promoter, and in certain of these embodiments increased autoantigen expression results in improved efficacy, including for example vaccine efficacy. In certain embodiments, the SPI2 promoter controlling expression of the autoantigen is an endogenous SPI2 promoter. In these embodiments, the exogenous nucleic acid encoding the autoantigen is inserted into the *Salmonella* genome in such a way that it is under the control of one or more endogenous SPI2 promoters. In other embodiments, the autoantigen may be under the control of an exogenous SPI2 promoter. In these embodiments, the exogenous nucleic acid encoding the autoantigen and the exogenous SPI2 promoter may be inserted into the *Salmonella Salmonella* as part of a single construct. In certain embodiments, the SPI2 promoters may be active in the *Salmonella typhi* strain, Ty21a.

In certain embodiments of the attenuated *Salmonella* bacteria provided herein, the autoantigen may be expressed as a fusion protein comprising all or a portion of a second protein. In certain of these embodiments, the autoantigen and the second protein are both exogenous, and in certain of these embodiments both are encoded by a single exogenous nucleic acid (i.e., as part of a single construct). In other embodiments, the nucleic acid encoding the second protein may be endogenous. For example, the exogenous nucleic acid encoding the autoantigen may be inserted into the *Salmonella* genome adjacent to an endogenous gene, such that the autoantigen is expressed as a fusion protein with the endogenous protein product. In certain of these embodiments, expression of both fusion protein components is under the control of the SPI2 promoter. Examples of suitable second proteins for use in autoantigen fusion proteins include SPI2-T3SS effector proteins such as SseF, SseJ, SseL, SifA, and SteC (Hegazy 2012). In certain embodiments, these second proteins function as fusion translocators for the autoantigen.

In certain embodiments of the attenuated bacteria provided herein, the exogenous nucleic acid encoding the autoantigen is under the control of one or more regulatory elements in addition to the SPI2 T3SS promoter, including for example one or more initiation codons, stop codons, or polyadenylation signals. These additional regulatory elements may be endogenous or exogenous. In those embodiments where the additional regulatory elements are exogenous, they may be introduced into the bacterium as part of the same expression construct as the exogenous autoantigen. In certain embodiments, the regulatory elements may be specifically selected for the cells in which the autoantigen will be expressed.

In certain embodiments of the attenuated bacteria provided herein, the bacteria further comprise one or more exogenous nucleic acids encoding immunomodulators, which as used herein refers to any substance which regulates the immune system. Examples of suitable immunomodulators include, without limitation, tolerogenic cytokines and immune hormones that suppress the reaction against non-self antigens. As set forth in the experimental results below, expression of the tolerogenic cytokine TGFβ enhanced the glucose lowering and anti-diabetic effects of exogenous autoantigens. Therefore, a suitable immunomodulator for use in the compositions disclosed herein is TGFβ. Other suitable immunomodulators include, for example, interleukin-10 (IL-10), interleukin-4 (IL-4), interleukin-27 (IL-27), all-trans retinoic acid (ATRA), and specific antibodies or antibody regions. Expression of the exogenous immunomodulators may be under the control of one or more exogenous or endogenous regulatory elements. In certain embodiments, the nucleic acid encoding the autoantigen and the nucleic acid encoding the immunomodulator may share one or more regulatory elements, such that expression of one corresponds to expression of the other.

In certain embodiments, the nucleic acid sequence encoding the autoantigen may be codon optimized for a particular organism (e.g., *Homo sapiens*) to enhance protein expression of the autoantigen. In certain embodiments, the nucleic acid sequence encoding the immunomodulator may be codon optimized for a particular organism (e.g., *Homo sapiens*) to enhance protein expression of the immunomodulator.

In certain embodiments, the attenuated *Salmonella* bacteria provided herein are *Salmonella enterica*, and in certain of these embodiments the *Salmonella* bacteria are *Salmonella enterica* serovar *Typhimurium* or *Salmonella enterica* serovar *Typhi*. Attenuation of the *Salmonella* bacteria is achieved by deleting or disrupting one or more endogenous *Salmonella* genes. Disruption of a gene may refer to any alteration to the gene or regulatory elements associated therewith that prevent the gene from being expressed or prevent the gene from being expressed at normal levels (e.g., mutation, deletion of one or more regulatory elements, truncation of the coding sequence, etc.). In certain embodiments, attenuation may be achieved by deleting or disrupting one or more endogenous genes involved in aromatic amino acid synthesis, purine biosynthesis, regulation of *Salmonella* virulence, or carbohydrate or amino acid metabolism. Specific examples of genes that may be deleted or disrupted in the attenuated *Salmonella* bacteria provided herein include, but are not limited to, aroA, purA, adenylate cyclase (cya), chorismate synthase (aroC), 3-dehydroquinase (aroD), stress protein HtrA, or the 5'-phosphoribosyl-glycinamide (GAR) synthetase PurD. In certain embodiments, the attenuated *Salmonella* bacteria are the double attenuated *Salmonella typhimurium* strains htrA/purD or htrA/gale or the aroA (SL7207) single mutant. In other embodiments, the attenuated *Salmonella* bacteria is *Salmonella typhi* strain Ty21a.

Provided herein in certain embodiments are methods of making the attenuated *Salmonella* bacteria provided herein. These methods comprise inserting an exogenous nucleic acid encoding an autoantigen into an attenuated *Salmonella* such that expression of the autoantigen is under the control of an endogenous or exogenous SPI2 promoter. In certain embodiments, these methods further comprise inserting an exogenous nucleic acid encoding an immunomodulator, such that expression of the immunomodulator is under the expression of the same or a different promoter than the autoantigen.

In certain embodiments, the *Salmonella* bacteria provided herein comprise at least one exogenous nucleic acid encoding an autoantigen or an immunomodulator that has been integrated into the chromosome of the bacteria. In these embodiments, the integration of the at least one exogenous nucleic acid into the bacterial chromosome may be performed according to the methods described in Husseiny 2005b.

Provided herein in certain embodiments are pharmaceutical formulations, including vaccine formulations, comprising one or more of the attenuated *Salmonella* bacteria disclosed herein. In certain of these embodiments, the attenuated *Salmonella* bacteria in these pharmaceutical formulations comprise one or more exogenous nucleic acids encoding an immunomodulator and one or more exogenous nucleic acids encoding autoantigen (i.e., autoantigen and immunomodulator are expressed by the same *Salmonella* vector). In other embodiments, the attenuated *Salmonella* bacteria in the pharmaceutical formulations provided herein do not comprise an exogenous nucleic acid encoding an immunomodulator. In these embodiments, the pharmaceutical formulation may comprise one or more immunomodulators, or one or more additional *Salmonella* or non-*Salmonella* vectors comprising a nucleic acid encoding an immunomodulator. In certain embodiments, the pharmaceutical formulations provided herein further comprise one or more pharmaceutically acceptable carriers. In certain embodiments, the pharmaceutical formulations provided herein further comprise one or more additional therapeutic agents or vectors comprising nucleic acids encoding one or more therapeutic agents.

Provided herein in certain embodiments is the use of the attenuated *Salmonella* bacteria disclosed herein or pharmaceutical formulations thereof to treat an autoimmune disorder, as well as the use of these attenuated bacteria and pharmaceutical formulations thereof in the manufacture of a medicament for treating an autoimmune disorder. In certain embodiments, the autoimmune disorder is T1D, rheumatoid arthritis (RA), Lupus erythematosus, muscular dystrophy, Grave's disease, or another autoimmune disorder for which an autoantigen may be obtained.

As disclosed herein, co-expression of autoantigen and immunomodulator was found to prevent the onset of diabetes in a mouse T1D model. As such, provided herein in certain embodiments are methods of treating an autoimmune disorder in a subject in need thereof by delivering to the subject one or more autoantigens and one or more immunomodulators.

As disclosed herein, co-expression of autoantigen and immunomodulator was found to preserve functional beta cell mass and reduce severe insulitis. As such, provided herein in certain embodiments are methods of preserving beta cell mass in a subject in need thereof by delivering to the subject one or more autoantigens and one or more immunomodulators. In certain embodiments are methods of reducing severe insulitis in a subject in need thereof by delivering to the subject one or more autoantigens and one or more immunomodulators.

Several studies have suggested a direct relationship between different cytokines and the induction of mucosal tolerance in NOD mouse and the results provided herein show significant increases in serum levels of IL2 and IL10 after combined vaccine therapy. As shown in the Example below, in mice who did not respond to therapy there was a significant increase in IL12(p70) and elevation of IL2 and IFNγ. However, specific effects to these molecules were not assigned since their activities depend on context. For example, IL2 is necessary for the expansion and differentiation of CTLs and many immunosuppressives act by blocking IL2 production or signaling, but IL2 also has a critical role in promoting $CD4^+ CD25^+ T_{reg}$ cell survival and function (Malek 2004) and T1D is associated with defects in IL2 pathway (Hulme 2012). IL10 alone has contradictory effects in NOD mice (Takiishi 2012; Goudy 2003; Pennline 1994; Balasa 2000; Balasa, Van Gunst 2000), and it may be context-specific. In summary, increased levels of IL2 and IL10 in response to combined therapy are consistent with a shift toward tolerance. As such, provided herein in certain embodiments are methods of increasing serum levels of IL2 and IL10 in a subject in need thereof by delivering to the subject one or more autoantigens and one or more immunomodulators.

In certain embodiments, the methods of treatment provided herein comprise administering to a subject in need thereof one or more attenuated *Salmonella* bacteria as disclosed herein, or a pharmaceutical formulation thereof. In certain of these embodiments, administration of the bacteria results in expression of a therapeutically effective amount of one or more autoantigens in the subject. In certain embodiments, the *Salmonella* bacteria administered to the subject comprise one or more exogenous nucleic acids encoding an immunomodulator (i.e., autoantigen and immunomodulator are delivered by the same *Salmonella* vector), and in certain of these embodiments administration of the bacteria results in expression of a therapeutically effective amount of one or more immunomodulators and one or more autoantigens. In other embodiments, immunomodulator expression is achieved by administering to the subject one or more additional *Salmonella* or non-*Salmonella* vectors encoding an immunomodulator. A non-*Salmonella* vector for use in these embodiments may be a bacterial vector other than *Salmonella* or a non-bacterial vector such as a plasmid. For example, in certain embodiments, the plasmid may be a mammalian expression plasmid. In other embodiments, the vector may be a bacterial vector such as a plasmid. In certain embodiments, the plasmid may be a balanced lethal plasmid system. For example, the plasmid may be a plasmid with asd-balanced lethal stabilization system as described in Galan et al (Galan 1990). In these embodiments, the methods comprise (a) administering one or more attenuated *Salmonella* bacteria as disclosed herein comprising an exogenous nucleic acid encoding an autoantigen and (b) administering one or more *Salmonella* or non-*Salmonella* vectors comprising an exogenous nucleic acid encoding an immunomodulator. In certain embodiments, expression of the immunomodulator in combination with the autoantigen results in a local tolerogenic microenvironment and improved attenuation of the destructive autoimmune reaction versus expression of the autoantigen alone. In certain embodiments, this improved attenuation is additive, while in other embodiments the treatment effect of autoantigen in combination with immunomodulator is synergistic, i.e., greater than would be expected by a simple additive effect. In still other embodiments, immunomodulator is administered directly to the subject. In these embodiments, the methods comprise (a) administering one or more attenuated *Salmonella* bacteria as disclosed herein comprising an exogenous nucleic acid encoding an autoantigen and (b) administering one or more immunomodulators.

In certain embodiments, the methods of treatment provided herein are methods of vaccinating a subject in need thereof against an autoimmune disorder. The use of the attenuated *Salmonella* bacteria provided herein present several advantages over previously developed autoimmune vaccines. First, the autoantigen is expressed intracellularly, which prevents degradation and potentially prolongs treatment effect by allowing extended exposure of the host to the autoantigen. Second, the autoantigen effect is limited to a small subset of immune cells. Third, the attenuated bacteria are taken up by gut APCs, which are naturally tolerogenic.

A "subject in need thereof" as used herein with regard to an autoimmune disorder is a subject who is currently diagnosed with an autoimmune disorder or exhibiting one or more symptoms associated with an autoimmune disorder, has previously been diagnosed with or exhibited one or more symptoms associated with an autoimmune disorder, or has been classified as at risk of developing an autoimmune disorder based on disease-associated biomarker levels or one or more genetic or environmental risk factors.

"Treating" or "treatment" as used herein with regard to a disorder may refer to preventing the disorder, reducing or ending symptoms associated with the disorder, generating a complete or partial regression of the disorder, or some combination thereof "Preventing" or "prevention" as used herein with regard to a disorder may refer to total or partial prevention of the disorder or symptoms associated with the disorder. For example, "prevention" may refer to completely stopping the development of the disorder or its symptoms or to delaying the onset or development of the disorder, delaying the onset or development of symptoms associated with the disorder, or reducing the risk of developing the disorder. "Treating" as used herein encompasses vaccination. For example, "treating" encompasses a method of vaccinating against T1D by administering a bacterial vector encoding autoantigen alone or in combination with a vector encoding an immunomodulator.

In certain embodiments of the methods disclosed herein, vectors encoding autoantigen and/or immunomodulator are delivered to a subject orally. In other embodiments, the vectors may be delivered by any other appropriate administration route, for example intranasally or by injection at any suitable treatment site. In certain embodiments, oral administration results in a greater treatment effect than administration by other routes. Without being bound by any theory, this may be because autoantigens provided orally to the GALT tend to induce a tolerogenic effect compared with presentation by injection to the central immune system, resulting in a more protective cytotoxic effect. In those embodiments wherein immunomodulator is administered directly to a subject, the immunomodulator can be administered by any suitable route, including for example oral or parenteral administration.

Although the embodiments provided herein focus on attenuated *Salmonella* bacteria, other live bacterial vaccines can be used in conjunction with the formulations and methods provided herein. For example, the methods provided herein for treating autoimmune disorders via localized delivery of autoantigen and immunomodulators can be carried out using *Mycobacteria, Listeria, Legionella,* or *Brucella* vectors.

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1: *Salmonella* Autoantigen Vectors

Figure 2:
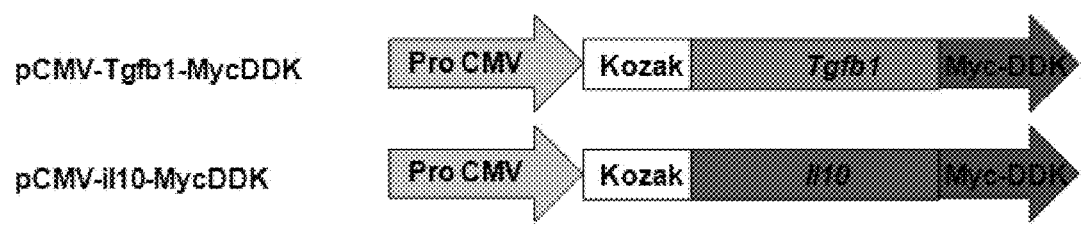
FIG. 2: Schematics of the immunomodulatory constructs pCMV-Tgfb1-MycDDK and pCMV-il10-MycDDK for expression and secretion of TGF-β and IL-10, respectively, by host cells.

In vitro assessment of *Salmonella*-based expression. The effect of orally delivered, *Salmonella*-expressed autoantigen on diabetes development and as a method of treatment of T1D was evaluated in a NOD mouse model. For generation of autoantigen-expressing *Salmonella* vectors, plasmids containing open reading frames (ORFs) for human GAD2 or mouse preproinsulin (Ins2) (Origene, Rockville, Md.) were inserted into the double attenuated *S. typhimurium* strain MvP728 (ΔhtrA/ΔpurD). Prior to insertion into MvP728, the GAD2 and Ins2 ORFs were subcloned into plasmid p2810. Both genes were fused in frame to *Salmonella* SseF, which mediates translocation to the host cytoplasm (Husseiny 2007), to produce a construct expressing an SseF/autoantigen fusion protein under the control of an SPI2-T3SS promoter. The resultant vectors were named pMH502 (containing GAD2) and pMH508 (Ins2) (FIG. 1). To provide local expression of immunomodulators, *S. typhimurium* MvP728 was transformed with plasmids containing the ORFs of two tolerogenic cytokines, Tgfβ1 and Il10 (Origene, Rockville, Md.), under the control of the cytomegalovirus (CMV) immediate early promoter (FIG. 2) for expression by the host cells.

Figure 3:
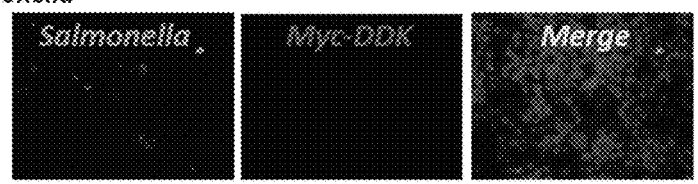
FIG. 3: *Salmonella*-based protein expression after macrophage infection. A. Control infection with *Salmonella* without expression plasmids. B. In vitro expression of recombinant protein antigens by *Salmonella* SPI2-T3SS. C. In vitro expression of tolerogenic cytokines, TGFβ and IL10, by host cells.
Figure 3:
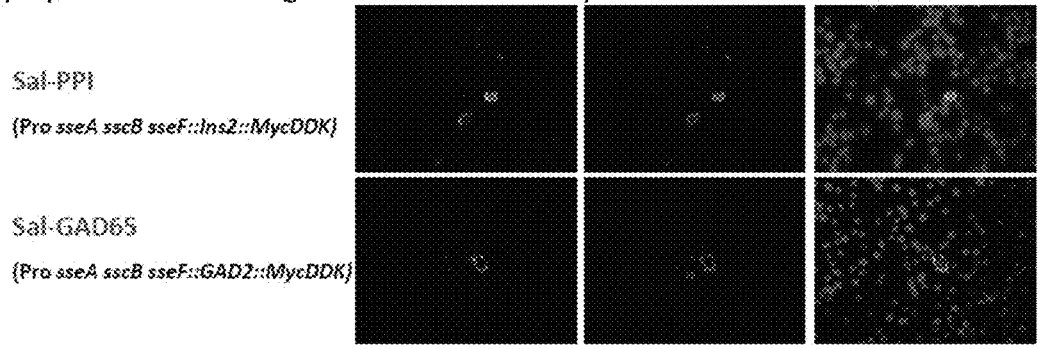
Figure 3:
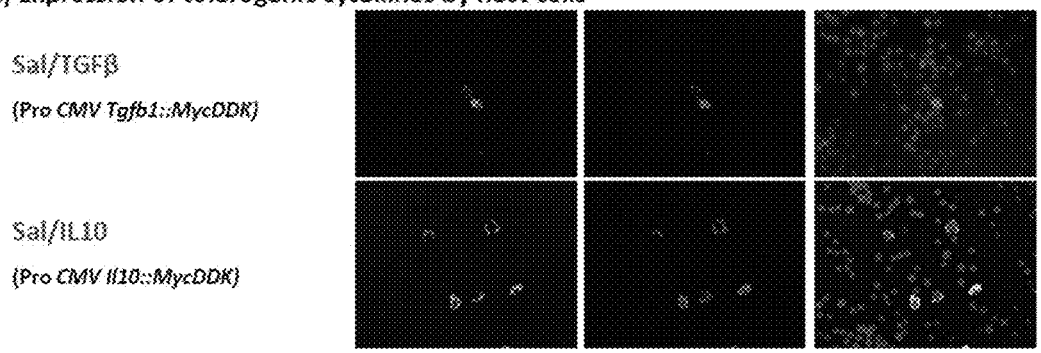

*Salmonella* transformed with the plasmids were used for in vitro infection of RAW264.7 macrophages followed by immunofluorescence staining (FIG. 3). As shown, all four strains of *Salmonella* were taken up by the macrophages in culture and are present in the cytoplasm (FIGS. 3B and 3C, see *Salmonella*, left column). In the case of the autoantigens the SPI2 promoter (PsseA) is activated after internalization of the bacteria by the macrophages causing expression of the fusion proteins. Infection with Sal-PPI (*Salmonella* expressing SseF-preproinsulin) or Sal-GAD65 (*Salmonella* expressing SseF-GAD65) results in appearance of the autoantigen (FIG. 3B, see Myc-DDK, center column) in the cytoplasm of the host cells which co-localizes with the bacteria (FIG. 3B, see Merge, right column). Conversely, *Salmonella* carrying plasmids for TGFβ (Sal/TGFβ) and IL10 (Sal/IL10) mediate host cell expression of cytokines (FIG. 3C, see Myc-DDK, center column) which co-localize with loci of intracellular bacterial replication (FIG. 3C, see Merge, right column). The results demonstrate that these constructs are competent to direct production of the respective proteins post-infection.

Prevention of Diabetes in NOD Mice Treated with Oral *Salmonella*-Based Vaccine.

Figure 4:
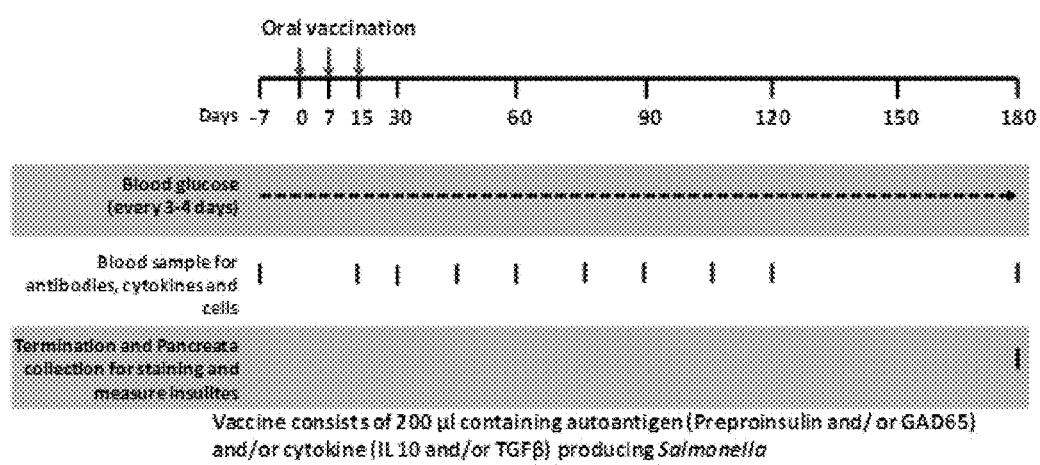
FIG. 4: Study design for evaluating the effects of combined autoantigen and immunomodulator therapy using *Salmonella* vector on glucose levels and diabetes development.
Figure 5:
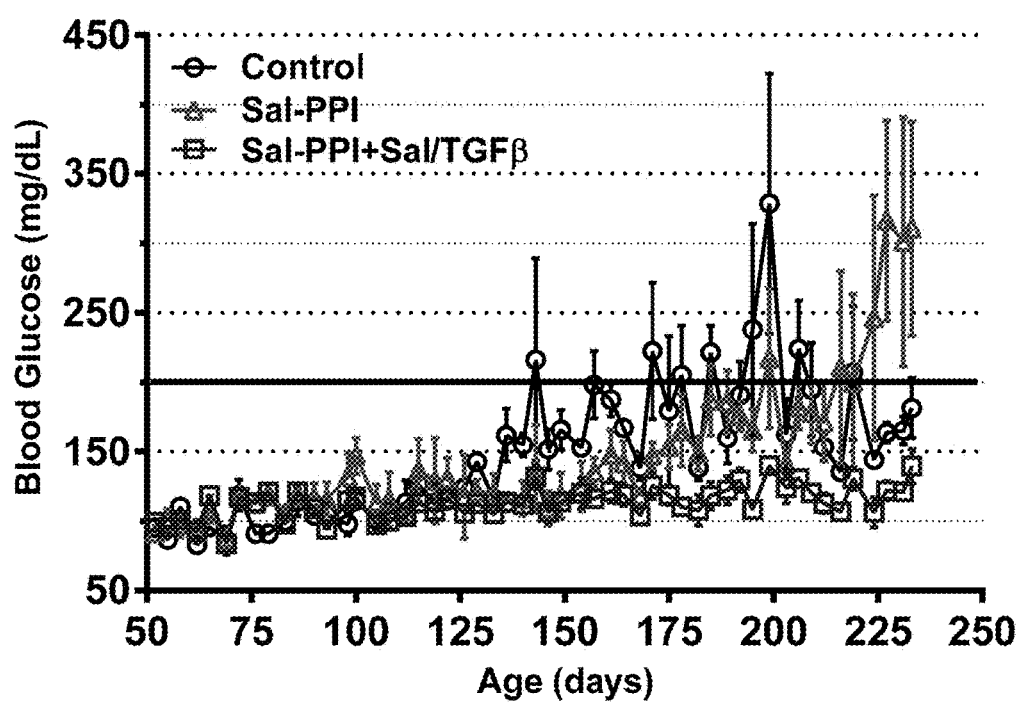
FIG. 5: Blood glucose levels at various timepoints in control NOD mice ("Control"; circle), NOD mice receiving *Salmonella* expressing autoantigen ("Sal-PPI"; triangle), and NOD mice receiving both *Salmonella* expressing autoantigen and *Salmonella* expressing immunomodulatory cytokine ("Sal-PPI+Sal/TGF-β"; square). The time points indicated are based on the age of the mice (days).
Figure 6:
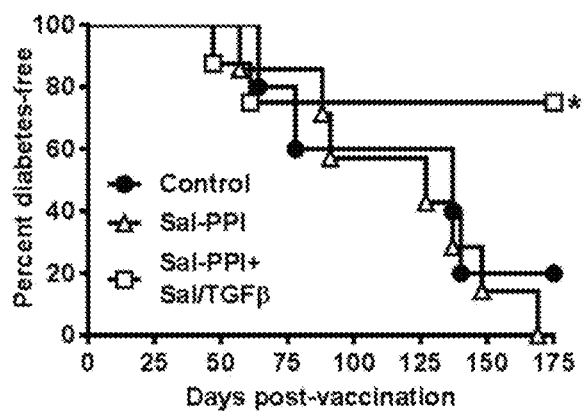
FIG. 6: NOD mice were treated orally with Sal-PPI combined with Sal/TGFβ (square), Sal-PPI alone (triangle), or with vehicle (circle). A. Log-rank plot of the percentage of non-obese diabetic (NOD) mice that remained diabetes-free over the time course of the study. The differences between the group of mice vaccinated with combined therapy and other groups was significant (p<0.05) by the log-rank (Mantel-Cox) test. B. The average of blood glucose levels at various time points. The time points indicated are based on the days post-vaccination. Statistical analysis using Two-way ANOVA shows the significance between combined therapy and control group (*P<0.05, P<0.005, *P<0.001, and ****P<0.0001), or antigen alone (#P<0.05, ##P<0.005, and ###P<0.001). C. The average of body weights for each group of mice over the time of the experiment. Each time point represents the mean and ±SEM of 5-8 samples.
Figure 6:
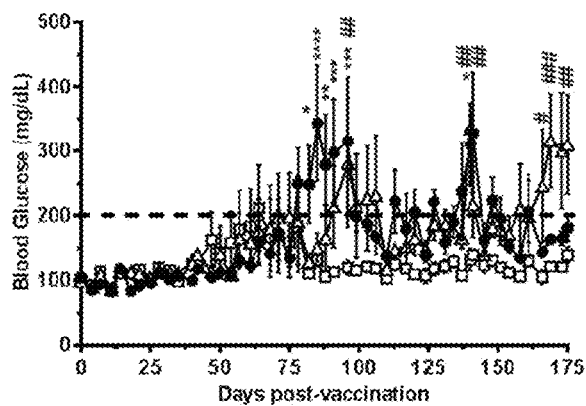
Figure 6:
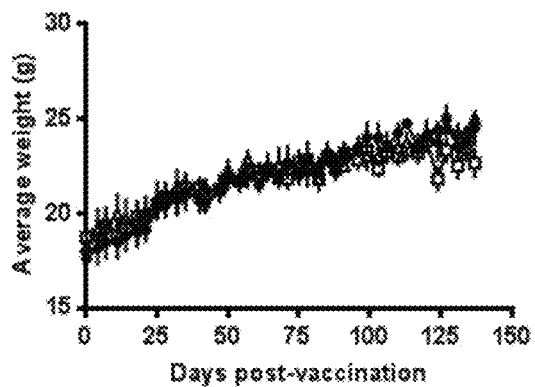

In vivo assessment of the vaccination methodology was tested using PPI as autoantigen in combination with TGFβ. Normoglycemic NOD mice (8 weeks) were treated orally for three consecutive weeks with Sal-PPI combined with or without Sal/TGFβ. Blood glucose level was monitored every 3 to 4 days. Control mice were treated with vehicle alone. The study timeline is summarized in FIG. 4. By day 85 after the first vaccination (day 58), blood glucose levels in control and autoantigen-only mice were highly unstable and had risen to diabetic or near diabetic levels. Mice receiving combined therapy with autoantigen vector and immunomodulator vector maintained normal blood glucose levels for more than 175 days (FIG. 5). FIG. 6A shows that combination therapy using Sal-PPI plus Sal/TGFβ prevented the development of T1D for more than 25 weeks in the majority of animals (75%), but only 20% of the control mice and no mice treated with Sal-PPI alone remained diabetes-free. In conjunction with this, blood glucose levels in control and antigen-alone vaccinated mice became highly unstable starting at day 75 post-vaccination, but remained stable throughout the study in mice treated with the combination therapy (FIG. 6B). The mice showed no signs of adverse effects of the vaccine and maintained normal weight gain throughout the study (FIG. 6C).

Intraperitoneal Glucose Tolerance Tests (IPGTT).

Figure 7:
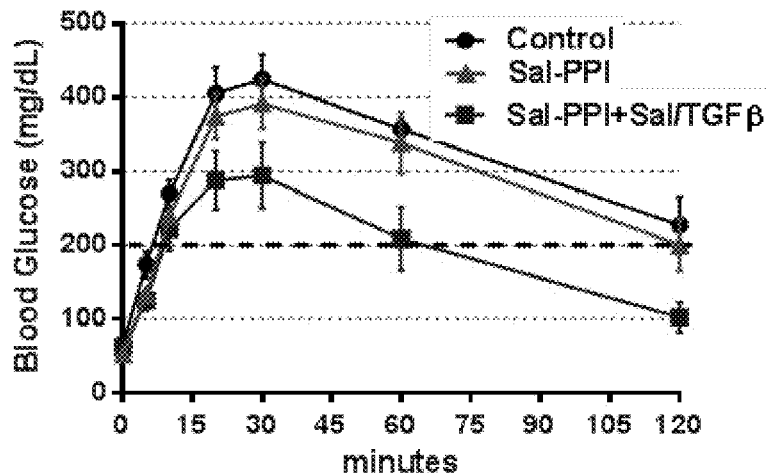
FIG. 7: Intraperitoneal glucose tolerance test (IPGTT) of NOD mice. A. Blood glucose levels at various timepoints following glucose injection in control mice (circle), mice receiving *Salmonella* expressing autoantigen ("Sal-PPI"; triangle), and mice receiving *Salmonella* expressing autoantigen and *Salmonella* expressing immunomodulatory cytokine ("Sal-PPI+Sal/TGF-β"; square). B. Area under the curve (AUC) calculations for the IPGTT showing resolution of glucose intolerance in Sal-PPI+Sal/TGFβ mice. AUC glucose was calculated over 120 minutes using fasting blood glucose as the basal level. C. Glucose clearance rates (k-values) for the IPGTT showing resolution of glucose intolerance in Sal-PPI+Sal/TGFβ mice. Glucose levels were measured at 30 minutes to the end of the assay at 120 minutes, k-value was calculated as the slope of the line from ln(BG) versus minutes. Asterisks indicate values that are significantly different from the group of mice vaccinated with combined therapy using statistical analysis of One-way ANOVA *$P<0.05$.
Figure 7:
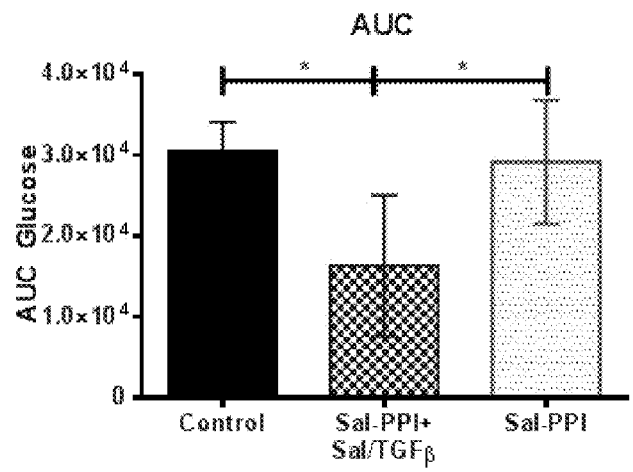
Figure 7:
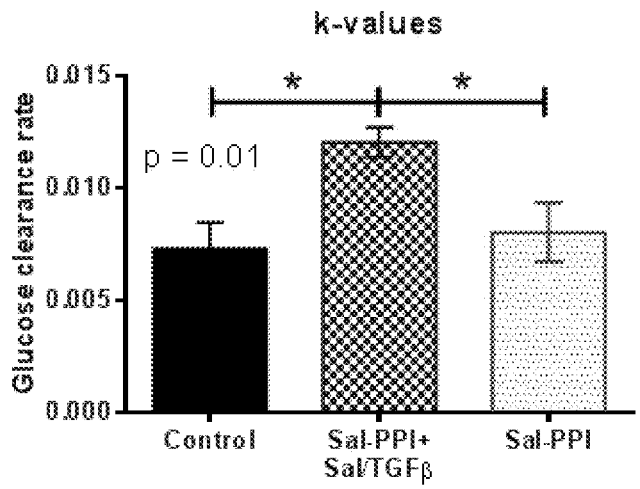

For evaluation of glucose tolerance and metabolic stability in each group of mice, an intraperitoneal glucose tolerance test (IPGTT) was performed at day 137 after vaccination. The peak post-injection blood glucose level in both control and antigen-alone groups occurred at 30 minutes with means of 424 and 392 mg/dL, respectively. Control mice or mice receiving autoantigen alone (Sal-PPI) were unable to maintain normal glucose levels even after 120 minutes and thus were shown to be glucose intolerant (FIG. 7A). Mice receiving autoantigen vector and immunomodulator vector (Sal-PPP+Sal/TGFβ, on the other hand, exhibited normal glucose metabolism (FIG. 7A); the average peak blood glucose level in co-vaccinated mice was 294 mg/dL and returned to normal by 120 minutes. Area under the curve (AUC) quantification of the results show that co-vaccination prevented the severe glucose excursions found in the other groups ($p<0.05$; FIG. 7B), and significantly improved the glucose disappearance rate (Saucier 1963; Amatuzio 1953) ($p=0.01$; FIG. 7C).

Co-Vaccination Preserved Functional β Cell Mass and Reduced Severe Insulitis.

Figure 8:
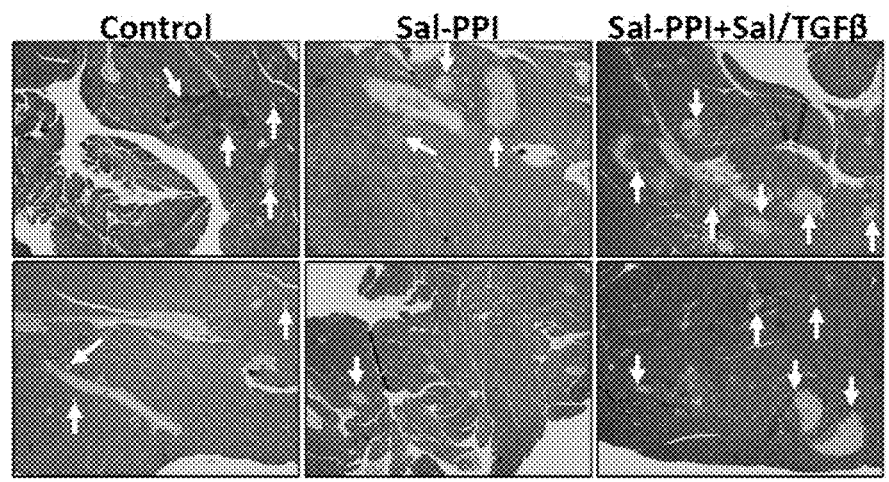
FIG. 8: Co-vaccination reduced severe insulitis and preserved insulin-positive cells. A. Pancreatic paraffin sections of the indicated groups were stained with hematoxylin and eosin (H&E). Islets were observed under light microscopy at 20× or 40×, enumerated and graded in a blinded fashion. B. Pancreatic samples were scored for islet infiltration as shown in the figure. Between 25 and 98 islets were scored from 4 mice of each group. The statistical significance was calculated with Two-way ANOVA for unpaired values and significance level indicated (p value) in comparison to the control group.
Figure 8:
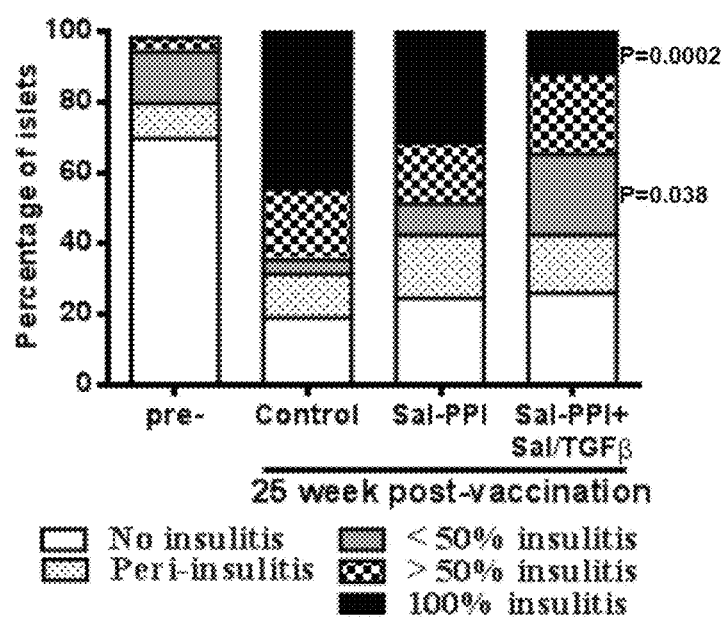

The level of lymphocyte infiltration was scored in paraffin sections from all treatment groups (FIG. 8A). Even prior to vaccination the mice exhibited insulitis (FIG. 8B). At 25 weeks post-treatment the unvaccinated control mice had severe insulitis consistent with the development of diabetes. Antigen alone (Sal-PPI) appeared to decrease insulitis overall but the change did not reach the level of significance and did not prevent diabetes. However, co-vaccination with Sal-PPI+Sal/TGFβ significantly reduced severe insulitis (FIG. 8B); Two-way ANOVA, p=0.038 at <50% and p=0.0002 at 100%), and preserved higher percentage islet area than control or antigen alone (ANOVA, p=0.048).

Figure 9:
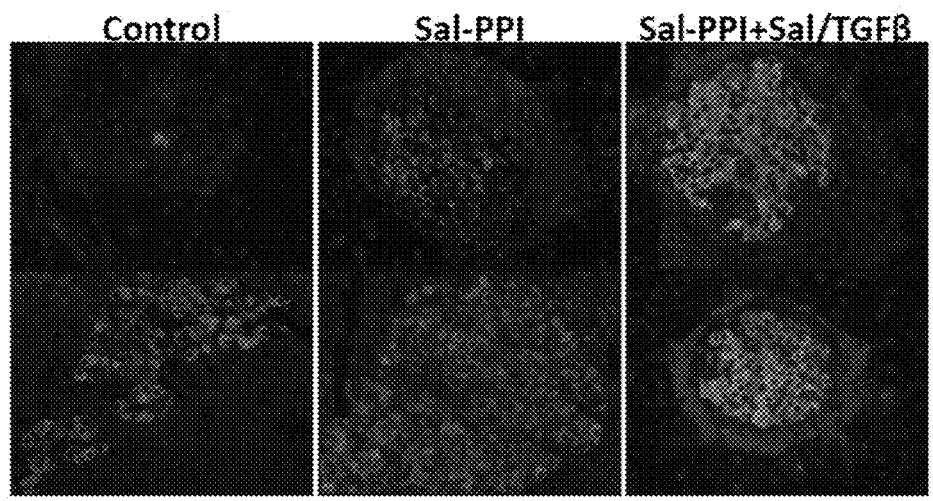
FIG. 9: A. Pancreatic paraffin sections of the indicated groups were immunostained for insulin and DNA. B. The fraction of beta cells was quantified in whole parallel sections and shown as the percentage of insulin positive cells in the total number of cells. The data display the mean of the percentage of insulin positive cells ±SEM. The statistical significance was calculated with One-way ANOVA for unpaired values and significance level indicated by asterisks (* $P<0.05$).
Figure 9:
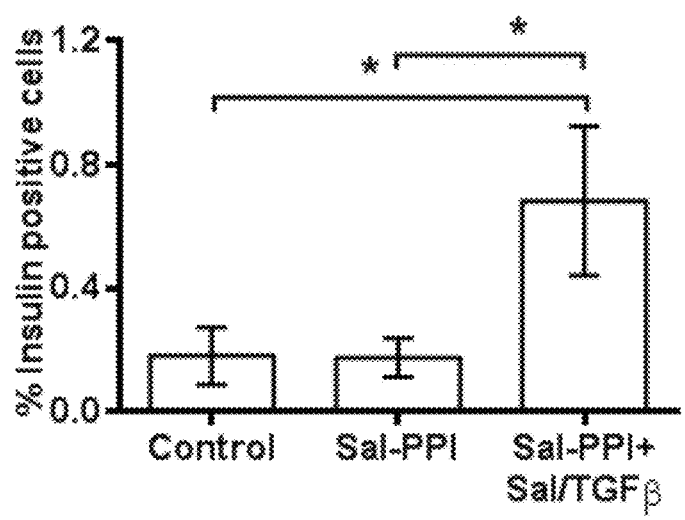

The percentage of insulin-positive cells was also quantified in the pancreas sections (FIGS. 9A and B). The islets in both the control and antigen alone groups exhibited abnormal morphology and low level insulin staining (FIG. 9A). The control in particular had islets with few or no insulin positive cells. By contrast, the combination treatment resulted in significantly higher percentages of insulin-positive cells compared to antigen alone and control (FIG. 9B; One-way ANOVA, p=0.049 and p=0.047, respectively).

Effect of Combined Therapy on Cytokine Profile.

Figure 10:
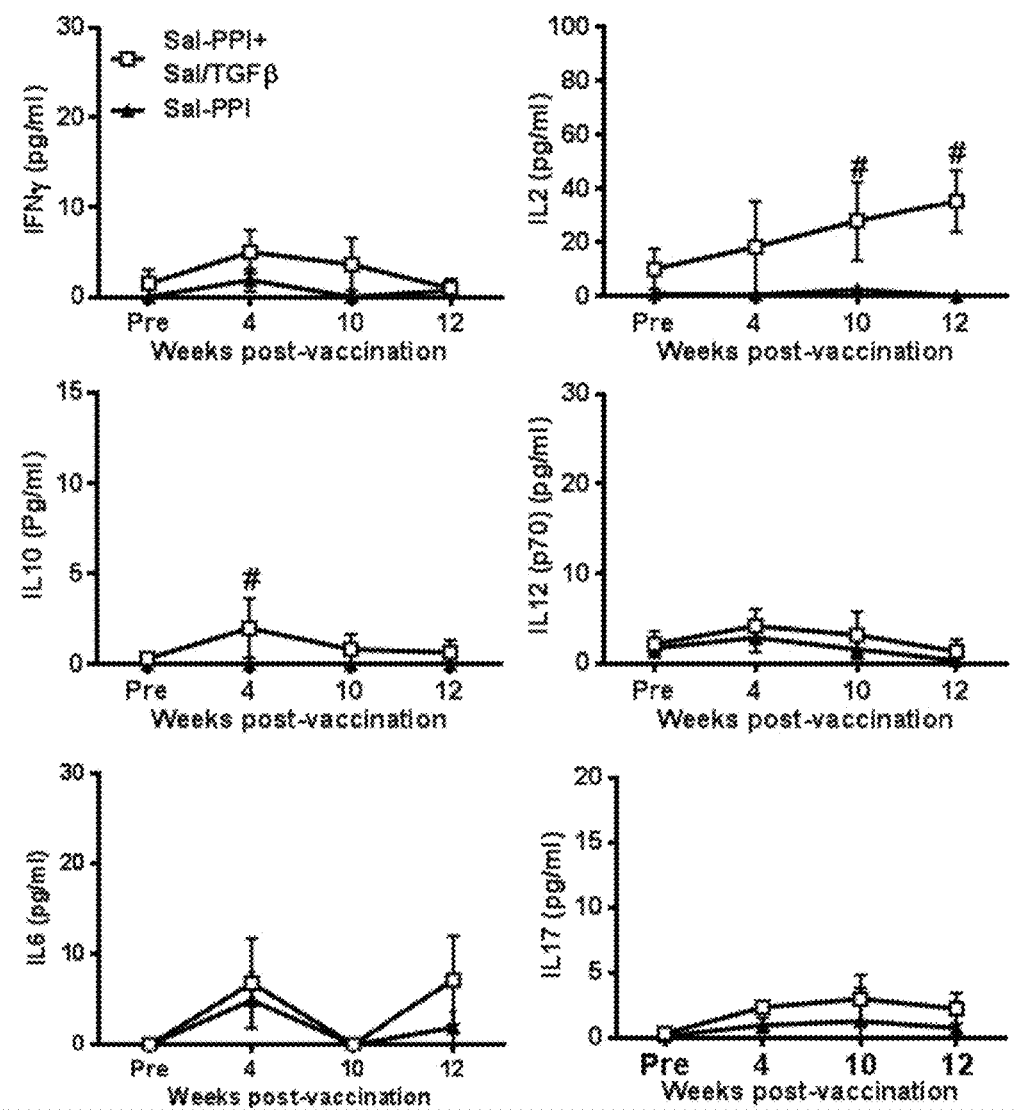
FIG. 10: Effect of combined therapy on serum cytokine levels. Serum was collected from groups of animals before (Pre-vac) and after (Post-vac) vaccination at the time indicated and the levels of IFNγ, IL2, IL12(p70), IL10, IL6 and IL17 were measured. Each time point represents the mean and ±SEM of 6 co-vaccinated mice (square) and 7 mice vaccinated with antigen alone (triangle).
Figure 11:
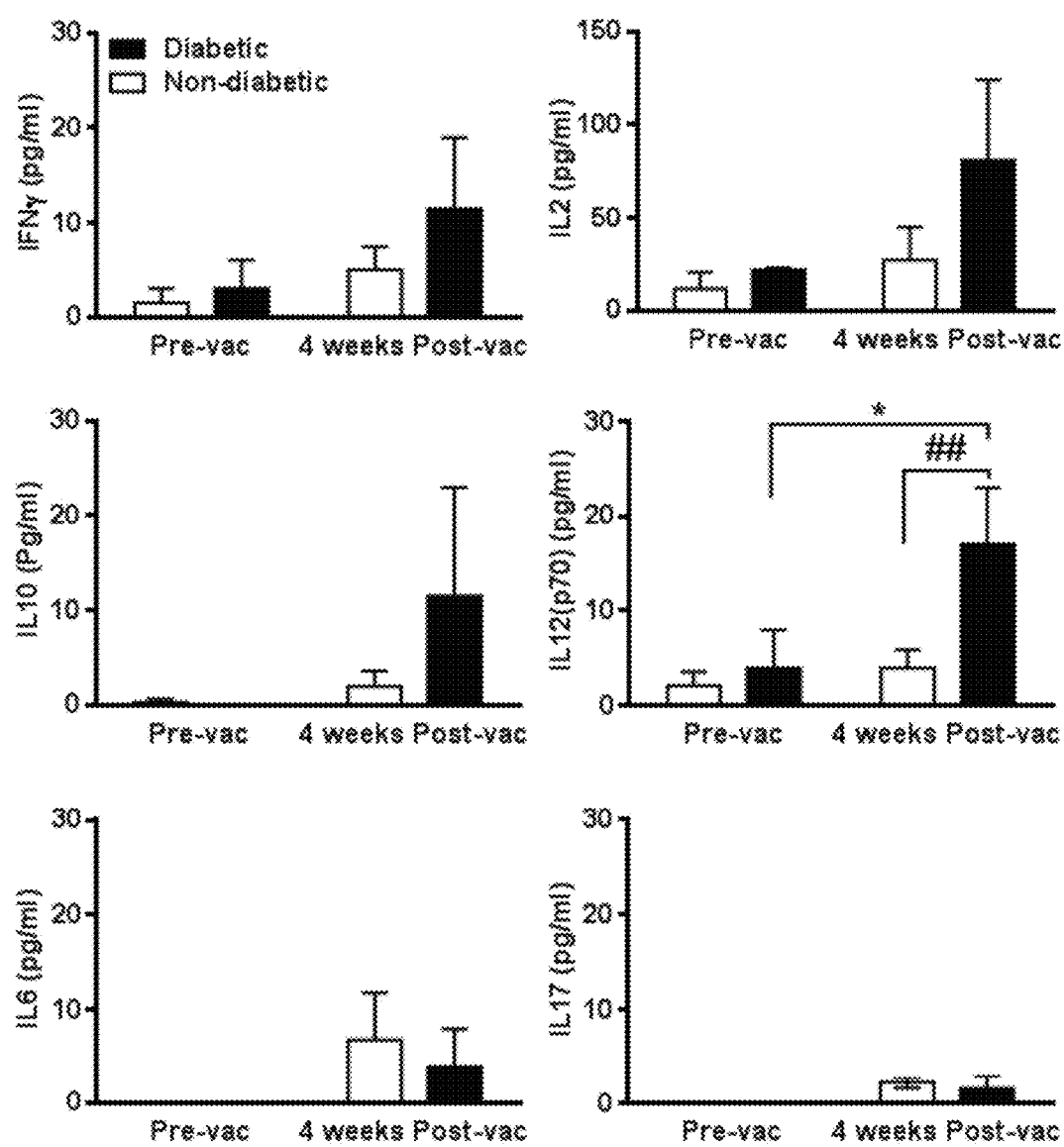
FIG. 11: Comparison of the cytokine levels between co-vaccinated diabetic (black bar) and non-diabetic mice (white bar). Significant differences were determined by Two-way ANOVA. *$P<0.05$ difference between pre- and post-vaccination. #$P<0.05$ differences between combined therapy and antigen alone.

To evaluate the effect of combined vaccine therapy on the immune response, cytokine levels in the serum were measured before and after vaccination. The combined therapy, but not antigen alone, increased serum levels of IL10 and IL2 (FIG. 10). IL10 rose to a significant level at 4 weeks post-vaccination and then returned to basal levels, but IL2 showed a significant increase for at least twelve weeks post-vaccination. In contrast, there was no significant effect on the levels of IL6, IL12(p70), IL17 or IFNγ. However, two of the co-vaccinated mice did not appear to respond to treatment, and comparison of responders (non-diabetic) and non-responders (diabetic) showed significant increases in serum levels of circulating IL12 in the diabetic animals, and elevation, though not significantly, of IL10, IL2, and IFNγ (FIG. 11).

These experiments will be repeated using autoantigens other than GAD65 and proinsulin and immunomodulators other than IL-10 and TGFβ. It is expected that other autoantigens, as well as various combinations of autoantigens and immunomodulators, will have similar effects, i.e., they will stabilize or lower blood glucose levels and provide protection against the development of diabetes. It is also expected that autoantigen delivered by this method could be readily combined with other immune interventions such as immunoablation or immunosuppression to provide effective treatments for autoimmune diseases.

Materials and Methods

Preparation of Salmonella Vaccines.

The double mutant strain of S. typhimurium MvP728 (ΔhtrA/ΔpurD) were used as previously described (Xiong 2010; Manuel 2011). Bacteria were cultured by growing to log phase in Luria-Bertani (LB), followed by quantitation by $OD_{600}$ and resuspension in 5% sodium bicarbonate to provide the appropriate dose in a total volume of 200 μL.

If required for selection, ampicillin (100 μg/ml), kanamycin and/or carbenicillin (50 μg/ml) was added. Plasmids containing the open reading frames (ORFs) for mouse Ins2 (cat#-MR226647), human GAD2 (cat#-RC225984), mouse Tgfb1 (cat#-MR227339) and mouse Il10 (cat#-MR2270340) were obtained from Origene (Rockville, Md.). The Tgfb1 and Il10 plasmids were used as is. The ORFs of Ins2 and GAD2 were sub-cloned into plasmid p2810 for expression under the control of the SPI2 promoter as a fusion protein with SseF which mediates translocation to the host cell cytoplasm (Husseiny 2007). Deep-Vent DNA polymerase (NEB) was used to amplify the mouse Ins2 gene using oligonucleotides INS2-HpaI-For (SEQ ID NO:1: 5'-ATAGTTAACATAGGGCGGCCGGGAATTC-3') and Myc-DDK-XbaI-Rev (SEQ ID NO:2: 5'-TCGTCTAGAT-TAAACCTTATCGTCGTCATCCTTGT-3') and human GAD2 gene using H-GAD65-HpaI-For1 (SEQ ID No:3: 5'-ATAGTTAACATGGCATCTCCGGGCTCTG-3') and Myc-DDK-XbaI-Rev from the Origene plasmids. The PCR fragments were sub-cloned into p2810 plasmid. The resulting plasmids pMH508 (preproinsulin) and pMH502 (GAD65) were confirmed by DNA sequencing and transformed into Salmonella MvP728 by electroporation (Bio-Rad MicroPulser).

In Vitro Infection.

The SPI2-T3SS promoter is inducible in vitro by low phosphate media (Husseiny 2005a). To evaluate autoantigen expression in vitro, bacteria were cultured in inducing or non-inducing media. The murine RAW264.7 macrophage cell line was obtained from the American Type Culture Collection (ATCC#-TIB-71), and maintained according to manufacture instructions. Cultures were treated with Salmonella-expressing preproinsulin pMH508 (Sal-PPI) or GAD65 pMH502 (Sal-GAD65), or Salmonella-delivering TGFβ (Sal/TGFβ) or IL10 (Sal/IL10) at a multiplicity of infection of 10 for 25 minutes, washed, and cultured for 16-20 hours for expression analysis (Husseiny 2007). Antigen expression was measured by Western blotting and immunofluorescent staining (Xiong 2010) with specific antibodies for Salmonella LPS, DDK tag and DAPI staining of nuclei followed by analysis with Olympus IX51 fluorescent microscope equipped with an infinity 2 camera (Olympus America, Melville, N.Y.). Pictures were captured using Infinity Analyze acquisition 5.0 software (Lumenera Corporation, Ottawa, Canada).

Animal Experiments.

Seven week old female NOD/ShiLtJ mice were obtained from The Jackson Laboratory (Bar Harbor, Me.) and maintained under specific pathogen-free conditions. Animals received high quality care consistent with Public Health Service Policy.

Normoglycemic NOD mice (8 weeks old) were grouped into 3 groups: Sal/TGFβ and Sal-PPI (n=8), Sal-PPI alone (n=7), and vehicle control (n=5). For mice receiving both autoantigen and immunomodulator vectors, the vectors were mixed together prior to administration. Mice administered vehicle alone were used as a mock control. Mice were vaccinated by oral gavage using a 20 G gavage needle (Cadence, Staunton, Va.) with $10^7$ CFU/mouse of Sal/TGFβ and/or $10^5$ CFU/mouse of Sal-PPI in a total volume of 200 μl of 5% sodium bicarbonate on days 0, 7, and 14. Mice were vaccinated in groups of 8.

Blood samples were drawn one week prior to vaccination (day −7) and at days 15, 30, 45, 60, 75, 90, 105, 120, and 180 after vaccination for antigen-specific antibody, cytokine, and cell population analysis. For antigen-specific antibody analysis, 96-well Nunc-Immuno MaxiSorp assay plates (Nunc, Roskilde, Denmark) coated with specific antigens were incubated with serial dilutions of serum samples. Antigen-specific antibodies were detected with peroxidase-labeled anti-mouse secondary antibodies, and titers were determined by the last dilution with an optimal density at 490 nm of 0.1 units above negative controls. For cell population analysis, lymphocytes were stained with antibodies specific for CD4, CD8, CD25, and FoxP3 and quantified by fluorescence-activated cell sorting (FACS). For evaluation of antigen-specific cells, splenocytes were isolated at various time points and cultured in vitro in the presence or absence of antigenic peptides. Feces was collected at various time points to evaluate shedding of Salmonella. For this analysis, feces were resuspended in 1 mL phosphate-buffered saline, and serial dilutions were plated onto LB agar plates containing appropriate antibiotics. Bacterial shedding was evaluated by counting colonies at 48 hours. The study was terminated at day 180, and pancreatic, liver, splenic, and intestinal tissue were collected for evaluation of residual Salmonella. Organ homogenates were also resuspended (100 mg in 1 mL phosphate-buffered saline), and serial dilutions were plated onto LB agar plates to evaluate bacterial distribution. The log CFU per organ was determined by counting colonies at 48 hours.

Intraperitoneal Glucose Tolerance Tests (IPGTT).

Blood glucose was measured every 3-4 days with One Touch Ultra glucometer (LifeScan, Milpitas, Calif.). Mice were considered diabetic when two consecutive blood glucose values were at or above 200 mg/dl (11.1 mM). Intraperitoneal glucose tolerance tests (IPGTT) were done as previously described (Andrikopoulos 2008). On day 137 post-vaccination mice fasted overnight and IP injected with 2.4 g of glucose per kg.

Insulitis Score.

At the end of experiment, pancreatic paraffin sections were stained with hematoxylin and eosin (H&E). Islets were observed under light microscopy at 20× or 40×, enumerated and graded in blinded fashion. Pancreatic samples were scored for islet infiltration as follows (0=no insulitis; 1=peri-insulitis; 2=mild insulitis with <50% islet area affected; 3=invasive insulitis with >50% islet area affected, 4=invasive insulitis with 100% islet area affected). Between 25 and 98 islets were scored from 4 mice of each group.

Immunostaining and Cytometry.

Pancreatic paraffin sections were immunostained for insulin and DNA. Parallel sections were quantitated by laser scanning cytometry using an iCys laser scanning cytometer (LSC) (Compucyte, Westwood, Mass.) based on staining for nuclei (using a 405 laser) and insulin (using a 488 laser) essentially as described previously (Todorov 2010). The whole sections were scanned for each slide. The fraction of beta cells is shown as the percentage of insulin positive cells in the total number of cells.

Multiplex Cytokine Measurement.

Circulating levels of IL-2, IL-6, IL-10, IL-12p(70), IL-17 and interferon-gamma (IFNγ) were measured in serum using a Milliplex Map kit (Millipore, Billerica, Mass.) and a Bio-Plex analyzer (Bio-Rad, Hercules, Calif.) in accordance with the protocol of the manufacturer.

Statistical Analyses.

Statistics were performed using GraphPad Prism 6 software and a value of $p<0.05$ was considered significant.

Example 2: Clinical Use of *Salmonella* Autoantigen Vectors

Additional experiments may be performed in human subjects to further optimize the use of the *Salmonella* autoantigen vectors as described herein. This may entail testing of human subjects that are approximately 18 to 30 years of age. The human subjects may have had T1D for less than three months. Antigen specific Tregs and CD8+, autoantibody levels and insulin requirements may be tested. Additionally, preservation of stimulated c-peptide in Mixed Meal Tolerance Test as a surrogate of functional beta cell mass may be tested.

As stated above, the foregoing is merely intended to illustrate various embodiments of the present invention. The specific modifications discussed above are not to be construed as limitations on the scope of the invention. It will be apparent to one skilled in the art that various equivalents, changes, and modifications may be made without departing from the scope of the invention, and it is understood that such equivalent embodiments are to be included herein.

REFERENCES

All cited references are hereby incorporated by reference herein in their entirety.

1 Abrahams Cell Microbiol 8:728 (2006)
2 Amatuzio J Clin Invest 32:328 (1953)
3 Andrikopoulos Am J Physiol Endocrinol Metab 295:E132 (2008)
4 Attridge Vaccine 15:155 (1997)
5 Balasa J Immunol 165:284 (2000)
6 Balasa J Immunol 165:7330 (2000)
7 Bao Infection and Immunity 59:3841 (1991)
8 Cheminay Int J Med Microbiol 298:87 (2008)
9 Clemente-Caseares Cold Spring Harbor Perspectives in Medicine 2:a007773 (2012)
10 Coombes J Biol Chem 279:49804 (2004)
11 Coombes J. Exp Med 204:1757 (2007)
12 Coombes Nat Rev Immunol 8:435 (2008)
13 Curtiss Crit Rev Immunol 30:255 (2010)
14 Deiwick Mol Microbiol 31:1759 (1999)
15 Delong Diabetes 60:2325 (2011)
16 Denes Diabetes Technol Ther 12:649 (2010)
17 Denes Mol Biotechnol 34:317 (2006)
18 Evans J Virol 77:2400 (2003)
19 Forrest The Journal of Infection Diseases 166:210 (1992)
20 Galan Gene 94:29 (1990)
21 Gentschev Chemotherapy 53:177 (2007)
22 Goudy J Immunol 171:2270 (2003)
23 Grangette Vaccine 20:3304 (2002)
24 Hegazy Infect Immun 80:1193 (2012)
25 Herold Diabetologia 56:391 (2013)
26 Hjorth Clin Immunol 138:117 (2011)
27 Holmgren Nat Med 11:S45 (2005)
28 Hulme Diabetes 61:14 (2012)
29 Husseiny Infect Immun 73:1598 (2005b)
30 Husseiny Microbiol Res 163:605 (2008)
31 Husseiny Vaccine 23:2580 (2005a)
32 Husseiny Vaccine 25:185 (2007a)
33 Husseiny Vaccine 27:3780 (2007b)
34 Husseiny Vaccine 27:3780 (2009)
35 Jaensson J Exp Med 205: 2139 (2008)
36 Kantele Vaccine 9:428 (1991)
37 Ludvigsson Diabetes Metab Res Rev 25:307 (2009a)
38 Ludvigsson J Diabetes Sci Technol 3:320 (2009b)
39 Ludvigsson N Engl J Med 359:1909 (2008)
40 Malek Nat Rev Immunol 4:665 (2004)
41 Manuel Cancer Res 71:4183 (2011)
42 Moser F1000 Biol Rep 2:75 (2010)
43 Nicholas Discov Med 11:293 (2011)
44 Nishikawa J Clin Invest 116:1946 (2006)
45 Peakman Diabetes 59:2087 (2010)
46 Pennline Clin Immunol Immunopathol 71:169 (1994)
47 Raine J Immunol 177:2224 (2006)
48 Saucier Can Med Assoc J 88:123 (1963)
49 Saxena Microbiology 159:1 (2013)
50 Sevil Vaccine 26:1870 (2008)
51 Stadinski Nat Immunol 11:225 (2010)
52 Sun J Exp Med 204:1775 (2007)
53 Takiishi J Clin Invest 122:1717 (2012)
54 Todorov Transplantation 90:836 (2010)
55 Turley Proc Natl Acad Sci USA 102:17729 (2005)
56 Vindurampulle Infection and Immunity 71:287 (2003)
57 von Herrath Clinical and Experimental Immunology 172: 186 (2013)
58 Weiner Immunol Rev 241:241 (2011)
59 Wherrett Lancet 378:319 (2011)
60 Xiong Int J Cancer 126:2622 (2010)
61 Xu Infect Immun 78:4828 (2010)
62 Yang J Immunol 176:2781 (2006)
63 Zhang Curr Opin Immunol 20:111 (2008)

What is claimed is:

1. A method of treating an autoimmune disorder in a subject in need thereof comprising administering an attenuated *Salmonella* bacterium comprising a nucleic acid encoding a diabetic autoantigen and a nucleic acid encoding an immunomodulator, wherein expression of the diabetic autoantigen is under the control of an SPI2 promoter, and wherein administration of the attenuated *Salmonella* bacterium results in expression of the diabetic autoantigen and the immunomodulator in the subject.

2. The method of claim 1, wherein treatment of the autoimmune disorder results in modulation of the immune response.

3. The method of claim 2, wherein treatment of the autoimmune disorder results in vaccination against the autoimmune disorder.

4. The method of claim 1, wherein the diabetic autoantigen is selected from the group consisting of proinsulin, glutamic acid decarboxylase, islet-specific glucose-6-phosphatase, chromogranin A, islet amyloid polypeptide, heat shock protein 60, islet antigen 2, and zinc transporter-8.

5. The method of claim 1, wherein the attenuated *Salmonella* bacterium is administered by oral administration.

6. The method of claim 1, wherein the immunomodulator includes TGFβ, IL10, IL-4, IL-27, all-trans retinoic acid (ATRA), or an antibody.

* * * * *